United States Patent
Lin et al.

(10) Patent No.: US 10,111,775 B2
(45) Date of Patent: Oct. 30, 2018

(54) APPLICATOR FOR SUPERFICIAL CORNEAL MEDICAMENTS

(71) Applicant: 1039578 B.C. Ltd., Vancouver, BC (CA)

(72) Inventors: David Tat-Chi Lin, Vancouver (CA); Stephanie Lei-Ching Lin, Brooklyn, NY (US)

(73) Assignee: 1039578 B.C. Ltd, Vancouver, British Columbia ( * ) Notice: Subject to any disclaimer, the term of this patent is extended or adjusted under 35 U.S.C. 154(b) by 519 days.

(21) Appl. No.: 14/664,368

(22) Filed: Mar. 20, 2015

(65) Prior Publication Data
US 2016/0270956 A1 Sep. 22, 2016

(51) Int. Cl.
*A61M 35/00* (2006.01)
*A61F 9/00* (2006.01)
*A61F 9/008* (2006.01)

(52) U.S. Cl.
CPC ............ *A61F 9/0017* (2013.01); *A61F 9/008* (2013.01); *A61F 9/0026* (2013.01)

(58) Field of Classification Search
CPC .... A61F 9/0017; A61F 9/0008; A61F 9/0026; A61H 33/28
See application file for complete search history.

(56) References Cited

U.S. PATENT DOCUMENTS

| | | | |
|---|---|---|---|
| 4,834,727 A | 5/1989 | Cope | |
| D585,990 S | 2/2009 | Melcher | |
| 7,678,078 B1 * | 3/2010 | Peyman | A61F 9/0017 604/116 |
| 7,824,372 B1 * | 11/2010 | Kurup | A61F 9/0017 604/116 |
| 2006/0129113 A1 | 7/2006 | Merrick | |
| 2013/0211335 A1 * | 8/2013 | Paques | A61F 9/0017 604/187 |
| 2013/0253528 A1 * | 9/2013 | Haffner | A61F 9/0017 606/107 |
| 2014/0094759 A1 | 4/2014 | Mansfield | |

OTHER PUBLICATIONS

PCT International Search Report, Application No. PCT/CA2016/050312, dated Mar. 18, 2016.
International Preliminary Report on Patentability (Chapter 1 of the Patent Cooperation Treaty) received in corresponding International Application No. PCT/CA2016/050312 dated Oct. 5, 2017.

* cited by examiner

*Primary Examiner* — Ariana Zimbouski
(74) *Attorney, Agent, or Firm* — McCarthy Tetrault LLP

(57) ABSTRACT

An applicator for applying fluid medicaments to a corneal surface of a patient, after surgery, includes a circular, ring-shaped member. The ring member creates an aperture which extends between parallel planes, with a wall surrounding the aperture as well as upper and lower openings into the aperture. The wall around the aperture is tapered, and there is a hole that extends through the wall. A hollow shaft is connected in fluid communication with the hole in the wall through which a fluid can be injected into the aperture. A bubble of the fluid can then be cradled in the aperture by the wall, and held therein by surface tension across the lower opening of the aperture. An application of the fluid bubble onto the patient's eye requires only contact between the fluid bubble and the eye, with no need for contact between the applicator and the eye.

16 Claims, 2 Drawing Sheets

APPLICATOR FOR SUPERFICIAL CORNEAL MEDICAMENTS

FIELD OF THE INVENTION

The present invention pertains generally to systems and methods for applying fluid (liquid) drops to an exposed surface of a human eye. In particular, the present invention pertains to applicators for depositing drops of a liquid medicament on the corneal surface of a patient following a surgical procedure. The present invention is particularly, but not exclusively, useful as a disposable, non-contact device that applies a liquid medicament uniformly over a corneal surface area having predetermined dimensions.

BACKGROUND OF THE INVENTION

It is well known that very small amounts of fluid, when unrestrained, will form into droplets. Rain drops are a familiar example of this development, as are drops from a leaky faucet. It is also well known that the creation of drops is the result of a physical phenomenon known as surface tension.

By definition, surface tension is a property possessed by liquid surfaces whereby they appear to be covered by a thin elastic membrane in a state of tension. From a physical perspective, the phenomenon of surface tension is due to unbalanced molecular cohesive forces in the liquid near its surface. A consequence here is that only small volumes of liquid will form as drops. Nevertheless, because the cohesive forces are unbalanced, they can be easily disrupted. When this happens, the liquid from the drop is dispersed. For example, contact forces against the surface of a drop will cause the drop to quickly disperse.

Several situations can be envisioned wherein it is advantageous to apply only a small volume of a liquid onto a surface area. Of interest here are post-surgical, medical situations that leave internal tissues exposed, such as the well-known laser surgical procedure, photorefractive keratectomy (PRK). In particular, a consequence of PRK is that tissue of the corneal stroma is post-surgically exposed. The exposed area of tissue due to de-epithelialization of the cornea is necessarily rather small, e.g. less than about 9 mm diameter, but it requires immediate attention. Specifically, an application of the liquid medicament mitomycin C is needed to prevent haze. Heretofore, sponges have been widely employed for this purpose. The results, however, have been irregular and variable. This is typically due to sponge contact with the eye, and other ancillary issues that include spillage, trauma to the exposed tissue, infections due to contact, and uneven or incomplete coverage of the surgical area.

In light of the above, it is an object of the present invention to provide a fluid (liquid) medicament applicator that is capable of applying a liquid medicament uniformly over a corneal surface area having predetermined dimensions. Another object of the present invention is to provide a disposable applicator that is capable of accurately and precisely applying a liquid medicament onto a surface area without contacting the surface area with the applicator. Still another object of the present invention is to provide a liquid medicament applicator that is easy to use, is simple to manufacture, and is comparatively cost effective.

SUMMARY OF THE INVENTION

In accordance with the present invention, a fluid (liquid) medicament applicator is provided that includes a ring-shaped member. In particular, the ring member (annulus) is formed to have a tapered aperture. The import of this component is that the ring member will cradle (i.e. hold) a drop of the fluid medicament in its aperture until the medicament is to be applied. To do this, the taper of the aperture is dimensioned so that an opening of the aperture (i.e. lower end of the ring member) is sufficiently small to set up surface tension on the fluid medicament across the aperture. The intended consequence here is that the liquid medicament under surface tension will bulge outwardly beyond the ring member. A subsequent contact of the bulging liquid medicament with a surface area of the patient (e.g. corneal stroma) will disrupt cohesive forces in the liquid medicament and thereby allow the liquid medicament to disperse over the surface area.

Structurally, the fluid medicament applicator of the present invention includes an annulus (ring member) with an inner wall that surrounds an aperture. The annulus has an outer diameter, D, and it has a height, h. Also, at an upper edge of the annulus, the aperture inside the wall has an inner diameter, $d_{i-upper}$. At the lower edge of the annulus, the aperture has an inner diameter, $d_{i-lower}$. Another feature of the annulus (ring member) is that the wall is formed with a recess which surrounds the aperture midway between the upper edge and the lower edge. Further, the wall is formed with a hole which extends through the wall and into fluid communication with the recess.

A means for injecting a fluid (liquid) medicament into the aperture of the annulus includes an elongated, hollow shaft that is formed with a lumen which extends between a proximal end and a distal end of the shaft. The shaft also defines a shaft axis, and it is formed with a decreasing taper in a distal direction. A syringe, or similarly equivalent component known in the art, is connected with the proximal end of the shaft for the purpose of pumping fluid medicament through the lumen of the shaft, and through the hole in the wall of the annulus, into the aperture. This causes a bubble of fluid medicament to form in the aperture. As it is formed, the bubble is cradled in the aperture under the influence of surface tension, and is held in the aperture prior to an application of the fluid medicament.

Additional structural details for the applicator of the present invention involve the configurational and dimensional relationships that are established between specified components. For instance, it is to be appreciated that the annulus defines a ring plane. The annulus also defines a central axis that is centered on the aperture, perpendicular to the ring plane. With this in mind, the relative dimensions of $d_{i-upper}$ and $d_{i-lower}$ of the annulus can then be used to establish a taper angle, $\alpha$, for the wall of the annulus. For a preferred embodiment of the present invention, $d_{i-upper}$ is greater than $d_{i-lower}$ in order to establish a taper for the wall. This angle, $\alpha$, is measured relative to the taper central axis of the annulus (ring member) and it will preferably be in a range between 0° and 90°. In another configurational relationship the shaft axis is oriented at an angle, $\beta$, relative to the central axis. In this case the angle, $\beta$, is in a range between 20° and 60°.

Normally, in the manufacture of an applicator, $d_{i-lower}$ will be around 6 mm. In some instances, however, depending on physical characteristics of the fluid medicament, $d_{i-lower}$ may be as much as 8.75 mm. For circumstances wherein it may be necessary to produce and apply a 9 mm bubble, and $d_{i-lower}$ is less than 6 mm, the outside diameter, D, at the lower edge of the tapered ring member can be made to be greater than 9 mm (D>9 mm and $d_{i-lower}$<6 mm). For another alternate embodiment of the present invention, a grating can be attached to the ring member to extend across the aperture at the lower edge of the annulus (ring member).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
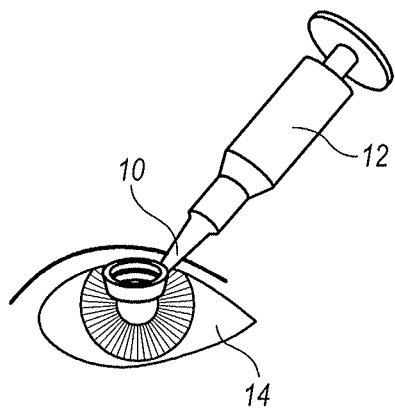
FIG. 1 is a perspective view of the fluid medicament applicator of the present invention being used in an intended operational environment.

Referring initially to FIG. 1, a fluid medicament applicator in accordance with the present invention is designated 10 and shown in its intended operational environment. In particular, the applicator 10 is shown attached to a syringe 12 (source of the fluid medicament). Also, as shown, the applicator 10 is positioned to drop fluid medicament into the eye 14 of a patient.

Figure 2:
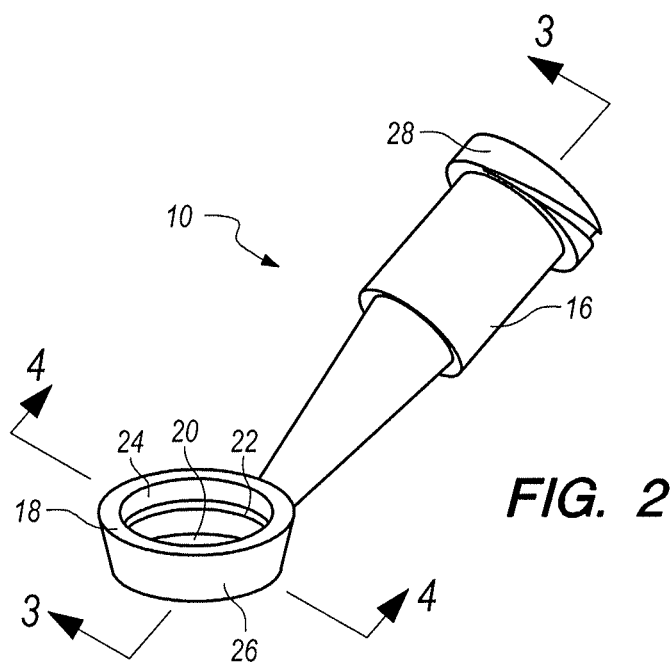
FIG. 2 is a perspective view of the fluid medicament applicator, enlarged to provide greater clarity for its operative components.

In FIG. 2 it will be seen that the applicator 10 includes a hollow shaft 16 which is affixed to an annulus (ring member) 18. FIG. 2 also shows that the annulus 18 is formed with an aperture 20, and that a recess 22 is formed into the annulus 18 to surround the aperture 20 between an upper edge 24 of the annulus 18 and a lower edge 26 of the annulus 18. Further, a luer lock 28 is shown in FIG. 2 which is used for attaching the applicator 10 to the syringe 12.

Figure 3:
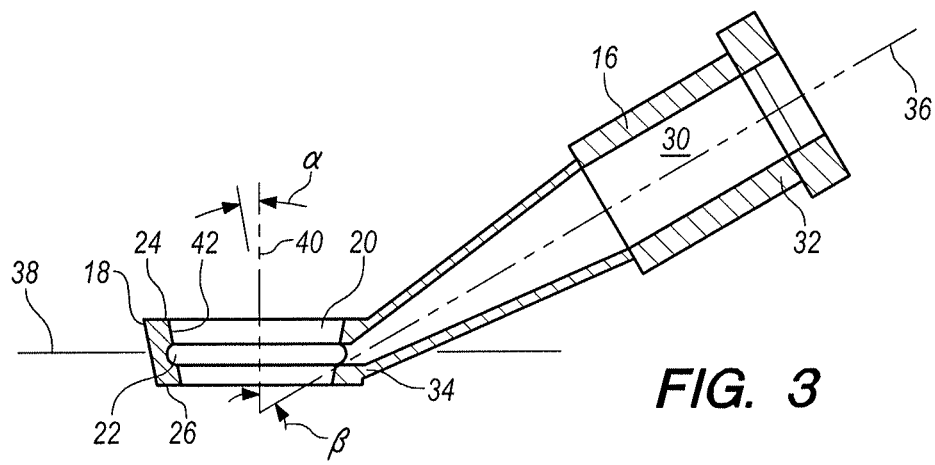
FIG. 3 is a cross-section view of the applicator as seen along the line 3-3 in FIG. 2.

A more detailed presentation of a preferred configuration for the applicator 10 is shown in FIG. 3. There it will be seen that the shaft 16 is formed with a lumen 30 extending from its proximal end 32 to its distal end 34. Also, the shaft 16 is shown to define a shaft axis 36. Further, FIG. 3 shows that the annulus 18 defines a ring plane 38 which lies midway between the upper edge 24 of the annulus 18 and its lower edge 26. Also, a central axis 40 is defined by the annulus 18 which is centered in the aperture 20 and is oriented perpendicular to the ring plane 38.

Still referring to FIG. 3 it is shown that the aperture 20 of the annulus (ring member) 18 has a taper which is defined by the taper angle, $\alpha$. More specifically, the taper angle, $\alpha$, is established between the side wall 42 of the annulus 18 that surrounds the aperture 20, and the central axis 40. Also, it will be seen in FIG. 3 that the hollow shaft 16 is angled relative to the central axis 40 by the angle, $\beta$. Dimensionally, for a preferred embodiment of the present invention, the taper angle, $\alpha$, for the side wall 42 of the annulus (ring member) 18 will be in a range between 0° and 90°, and the inclination angle, $\beta$, of the hollow shaft 16, relative to the annulus (ring member) 18, will be in a range between 20° and 60°.

Figure 4:
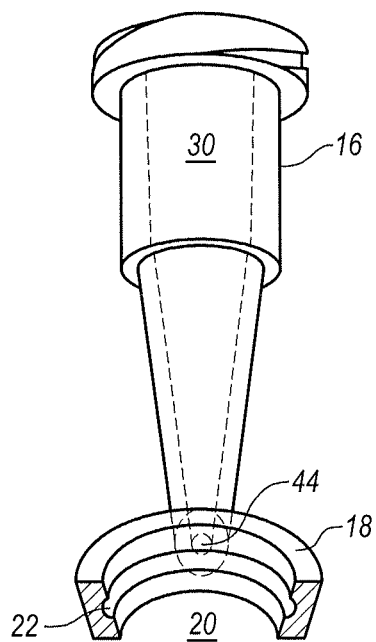
FIG. 4 is a cross-section view of the applicator as seen along the line 4-4 in FIG. 2.

FIG. 4 shows that the lumen 30 of the hollow shaft 16 is in fluid communication with the aperture 20 of the annulus 18 via a hole 44. Further, the hole 44 enters the aperture 20 at the recess 22. It is to be appreciated, however, that there may be more than one such recess 20 or, possibly, no recess 20. Moreover, the hole 44 need not enter the aperture 20 precisely at the recess 22.

Figure 5:
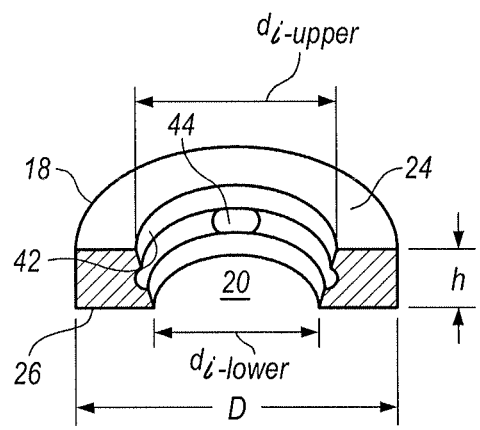
FIG. 5 is a cross-section view of an exemplary ring member (annulus) of the applicator as would be seen along the line 4-4 in FIG. 2, showing pertinent dimensions which can be varied to establish alternate embodiments for the present invention.

An appreciation of the various configurations envisioned for the annulus (ring member) 18 of the applicator 10 is possible by reference to FIG. 5. There it will be seen, in detail, that the aperture 20 is bounded by the side wall 42, by an upper opening (not numbered) which is circumscribed by the upper edge 24, and by a lower opening (not numbered) which is circumscribed by the lower edge 26. Within this structure the diameter of the upper opening of the aperture 20 is $d_{i\text{-}upper}$, and the diameter of the lower opening of the aperture is $d_{i\text{-}lower}$. Also, an outer diameter, D, for the annulus 18 is identified, and the height, h, of the annulus 18 is shown to be the distance between the upper edge 24 and the lower edge 26. With these various dimensions in mind, the present invention envisions that $d_{i\text{-}upper}$ will, preferably, be greater than $d_{i\text{-}lower}$. Thus, the taper angle, $\alpha$, will be greater than zero and, accordingly, the side wall 42 of the aperture 20 will be tapered. On the other hand, D can vary through the height, h, as desired. Consequently, D can be established (e.g. made greater) to help disperse a bubble of the fluid medicament as it is being applied.

Figure 6A:
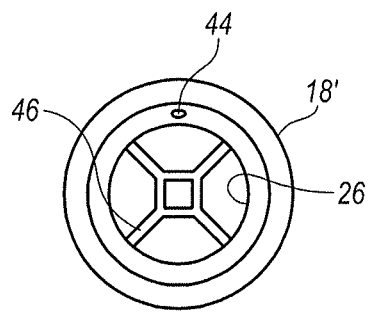
FIG. 6A is a top plan view of an alternate embodiment for the ring member (annulus) of the present invention showing the use of a grating across the aperture to facilitate surface tension.
Figure 6B:
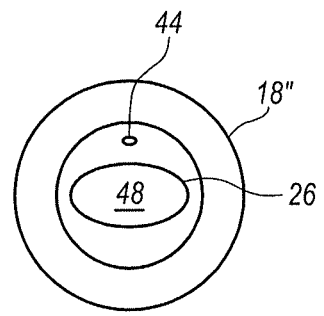
FIG. 6B is a top plan view of an alternate embodiment of the ring member (annulus) of the present invention showing the employment of an oval-shaped aperture.

FIGS. 6A and 6B show alternate embodiments for the applicator 10 of the present invention. In FIG. 6A, for a ring member 18', a grating 46 is shown employed across the circular bottom opening (not numbered) of the aperture 20. For a ring member 18", as shown in FIG. 6B, the bottom opening can be an oval 48.

While the particular Applicator for Superficial Corneal Medicaments as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A corneal applicator for applying a fluid medicament onto a corneal surface comprising:
   an elongated, hollow shaft comprising a lumen for holding the fluid medicament, the shaft having a proximal end and a distal end with the lumen extending therebetween, wherein the shaft defines a shaft axis and has a decreasing taper in a distal direction;
   a ring member connected with the shaft, wherein the ring member surrounds an aperture and defines a ring plane with a central axis centered in the aperture and perpendicular to the ring plane, and wherein the aperture of the ring member is in fluid communication with the lumen of the shaft; and
   an injection portion connected with the proximal end of the shaft configured to inject the fluid medicament into the aperture of the ring member to create a bubble of the fluid medicament held therein by surface tension across the aperture for depositing the fluid medicament onto the corneal surface.

2. The corneal applicator as recited in claim 1 wherein the ring member is tapered around the aperture to cradle the bubble of the fluid medicament in the aperture, and wherein the ring member is formed with at least one circular recess oriented in the ring plane, with the recess centered on the central axis.

3. The corneal applicator as recited in claim 2 wherein the ring member defines an upper plane and a lower plane, with the upper plane and the lower plane being parallel to the ring plane with the ring plane located midway therebetween, and wherein the ring member has an outer diameter, D, and the aperture has an inner diameter in the upper plane, di-upper, and an inner diameter in the lower plane, di-lower, wherein a taper angle, α, is established for the ring member when di-upper is greater than di-lower, and wherein the taper angle, α, for the ring member is measured relative to the central axis of the ring member and is in a range between 0° and 90°.

4. The corneal applicator as recited in claim 3 wherein D of the tapered ring member in the lower plane is greater than 9 mm and di-lower is less than 6 mm (D>9 mm and di-lower<6 mm).

5. The corneal applicator as recited in claim 3 further comprising a grating attached to the ring member, with the grating extending across the aperture in the lower plane.

6. The corneal applicator as recited in claim 3 wherein di-lower is in a range between 6 mm and 8.75 mm.

7. The corneal applicator as recited in claim 1 wherein the shaft axis is oriented at an angle, β, relative to the central axis and the angle, β, is in a range between 20° and 60°.

8. The corneal applicator as recited in claim 1 wherein the fluid medicament is injected via a syringe.

9. The corneal applicator as recited in claim 1 wherein the fluid medicament is mitomycin C, and the applicator is made of a medical grade plastic.

10. A corneal applicator for applying a fluid medicament onto a corneal surface comprising:
an annulus for defining an aperture bounded by a wall, wherein the wall has a height, h, and an outer diameter, D, and wherein the wall extends between an upper edge with an inner diameter, di-upper, and a lower edge with an inner diameter, di-lower, and wherein di-upper is greater than di-lower to establish a taper for the wall; and
an injection portion configured to inject a fluid medicament into the aperture of the annulus to cradle a bubble of the fluid medicament in the aperture to hold the bubble therein by surface tension for depositing the fluid medicament onto the corneal surface.

11. The corneal applicator as recited in claim 10 wherein the wall of the annulus is formed with a recess surrounding the aperture midway between the upper edge and the lower edge, and further wherein the wall is formed with a hole extending through the wall and into fluid communication with the recess for injecting the fluid medicament into the aperture.

12. The corneal applicator as recited in claim 10 wherein the injection portion comprises:
an elongated, hollow shaft comprising a lumen, the shaft having a proximal end and a distal end with the lumen extending therebetween, wherein the shaft defines a shaft axis and has a decreasing taper in a distal direction; and
a syringe connected with the proximal end of the shaft.

13. The corneal applicator as recited in claim 12 wherein the annulus defines a ring plane with a central axis perpendicular to the ring plane, and wherein the di-upper and di-lower establish an angle of taper, a, for the wall of the annulus, wherein a is measured relative to the central axis of the ring member and is in a range between 0° and 90°.

14. The corneal applicator as recited in claim 13 wherein D of the tapered ring member in the lower plane is greater than 9 mm and di-lower is less than 6 mm (D>9 mm and di-lower<6 mm).

15. The corneal applicator as recited in claim 13 further comprising a grating attached to the ring member, with the grating extending across the aperture in the lower plane.

16. The corneal applicator as recited in claim 13 wherein the shaft axis is oriented at an angle, β, relative to the central axis, and the angle, β, is in a range between 20° and 60°.

* * * * *